United States Patent [19]

Kaufman

[11] Patent Number: 5,457,107
[45] Date of Patent: Oct. 10, 1995

[54] POLYMORPHIC FORM OF A TACHYKININ RECEPTOR ANTAGONIST

[75] Inventor: Michael J. Kaufman, New Hope, Pa.

[73] Assignee: Merck & Co., Inc., Rahway, N.J.

[21] Appl. No.: 307,962

[22] Filed: Sep. 16, 1994

[51] Int. Cl.⁶ .................. A61K 31/535; C07D 413/06
[52] U.S. Cl. ........................... 514/236.2; 514/132
[58] Field of Search .................. 544/132; 514/236.2

[56] References Cited

FOREIGN PATENT DOCUMENTS 00440  1/1994  WIPO .

*Primary Examiner*—Robert W. Ramsuer
*Attorney, Agent, or Firm*—J. Eric Thies; David L. Rose

[57] ABSTRACT

This invention is concerned with a novel polymorphic form of the compound 2-(S)-(3,5-bis(trifluoromethyl)benzyloxy)-4-(3-(5-oxo-1H,4H-1,2,4-triazolo)methyl)-3-(S)-phenyl-morpholine which is a tachykinin receptor antagonist useful in the treatment of inflammatory diseases, pain or migraine, asthma, and emesis.

The instant polymorphic form has advantages over the other known forms of 2-(S)-(3,5-bis(trifluoromethyl)benzyloxy)-4-(3-(5-oxo-1H,4H-1,2,4-triazolo)methyl)-3-(S)-phenyl-morpholine in terms of thermodynamic stability and suitability for inclusion in pharmaceutical formulations.

2 Claims, No Drawings

POLYMORPHIC FORM OF A TACHYKININ RECEPTOR ANTAGONIST

SUMMARY OF THE INVENTION

This invention is concerned with a novel polymorphic form of the compound: 2-(S)-(3,5-bis(trifluoromethyl)benzyloxy)-4-(3-(5-oxo- 1H,4H-1,2,4-triazolo)methyl)-3-(S)-phenyl-morpholine.

The present invention is also concerned with pharmaceutical formulations comprising this novel polymorphic form of the compound as an active ingredient and the use of the compound and its formulations in the treatment of certain disorders.

The novel polymorphic form of this invention is a tachykinin receptor antagonist useful in the treatment of inflammatory diseases, pain or migraine, asthma, and emesis.

This polymorphic form has advantages over the other known forms of 2-(S)-(3,5-bis(trifluoromethyl)benzyloxy)-4-(3-(5-oxo-1H,4H-1,2,4-triazolo)methyl)-3-(S)-phenyl-morpholine in terms of thermodynamic stability and suitability for inclusion in pharmaceutical formulations.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 35, 85–141 (1983)). The NK1 and NK2 receptor subtypes are implicated in synaptic transmission (Laneuville et al., *Life Sci.*, 42:1295–1305 (1988)).

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, 199, 1359 (1978); P. Oehme et al., *Science*, 208, 305 (1980)) and plays a role in sensory transmission and pain perception (T. M. Jessell, *Advan. Biochem. psyhopharmacol.* 28, 189 (1981)). For example, substance P is believed to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter? *TIPS*, 8 506–510 (Dec. 1987)], specifically in the transmission of pain in migraine (see B. E. B. Sandberg et al., *Journal of Medicinal Chemistry*, 25, 1009 (1982); M. A. Moskowitz, *Trends Pharmacol. Sci.*, 13, 307–311 (1992)), and in arthritis (Levine, et al. *Science*, 226 547–549 (1984); M. Lotz, et al., *Science*, 235, 893–895 (1987)). Tachykinins have also been implicated in gastrointestinal (GI) disorders and diseases of the GI tract, such as inflammatory bowel disease [see Mantyh et al., [Neuroscience, 25 (3), 817–37 (1988) and D. Regoli in "Trends in Cluster Headache" Ed. F. Sicuteri et al., Elsevier Scientific Publishers, Amsterdam, pp. 85–95 (1987)], and emesis [*Trends Pharmacol. Sci.*, 9, 334–341 (1988), F. D. Tatersall, et al., *Eur. J. Pharmacol.*, 250, R5–R6 (1993)].

It is also hypothesized that there is a neurogenic mechanism for arthritis in which substance P may play a role [Kidd et al., "A Neurogenic Mechanism for Symmetric Arthritis" in *The Lancet*, 11 Nov. 1989 and Gronblad et al., "Neuropeptides in Synovium of Patients with Rheumatoid Arthritis and Osteoarthritis" in *J. Rheumatol.* 15(12) 1807–10 (1988)]. Therefore, substance P is believed to be involved in the inflammatory response in diseases such as rheumatoid arthritis and osteoarthritis [O'Byrne et al., *Arthritis and Rheumatism*, 33 1023–8 (1990)].

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti, *J. Auton. Pharmacol*, 13, 23–93 (1993); see also R. M. Snider, et al., Chem. Ind., 11, 792–794 (1991). Neurokinin-1 receptor antagonists alone or in combination with bradykinin receptor antagonists may also be useful in the prevention and treatment of inflammatory conditions in the lower urinary tract, especially cystitis [Giuliani, et al., *J. Urology*, 150, 1014–1017 (1993)]. Other disease areas where tachykinin antagonists are believed to be useful are allergic conditions [Hamelet et al., *Can. J. Pharmacol. Physiol.*, 66, 1361–7 (1988)], immunoregulation [Lotz, et al., *Science*, 241 1218–21 (1988), Kimball, et al., *J. Immunol.*, 141 (10) 3564–9 (1988); A. Perianin, et al., *Biochem. Biophys. Res Commun.* 161,520 (1989)], post-operative pain and nausea [C. Bountra, et al., *Eur. J. Pharmacol.*, 249, R3–R4 (1993), F. D. Tattersall, et al., *Neuropharmacology*, 33, 259–260 (1994)], vasodilation, bronchospasm, reflex or neuronal control of the viscera [Mantyh et al., *PNAS*, 85, 3235–9 (1988)] and, possibly by arresting or slowing β-amyloidmediated neurodegenerative changes [Yankner et al., *Science*, 250, 279–82 (1990)] in senile dementia of the Alzheimer type, Alzheimer's disease and Downs Syndrome. Substance P may also play a role in demyelinating diseases such as multiple sclerosis and amyotrophic lateral sclerosis [J. Luber-Narod, et. al., poster C.I.N.P. XVIIIth Congress, 28th Jun.–2nd Jul., 1992], and in disorders of bladder function such as bladder detrusor hyper-reflexia [*Lancet*, 16th May 1992, 1239]. Antagonists selective for the neurokinin-1 (NK-1) and/or the neurokinin-2 (NK-2) receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992); P. Barnes, et al., *Trends Pharmacol. Sci.*, 11,185–189 (1993)). Tachykinin antagonists may also be useful in the treatment of small cell carcinomas, in particular small cell lung cancer (SCLC) [Langdon et al., *Cancer Research*, 52, 4554–7 (1992)].

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus (EPO Publication No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EPO Publication No. 0,394,989).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, 16–19 May, 1993, published in *Am. Rev. of Respiratory Dis.*, May 1993].

In the recent past, some attempts have been made to provide peptide-like substances that are antagonists for the receptors of substance P and other tachykinin peptides in order to more effectively treat the various disorders and diseases mentioned above. For example Lowe, *Drugs of the Future*, 17 (12) 1115–1121 (1992) and EPO Publication Nos. 0,347,802, 0,401,177 and 0,412,452 disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. Merck U.S. Pat. No. 4,680,283 also discloses peptidal analogs of substance P. Certain inhibitors of tachykinins have been described in U.S. Pat. No. 0 4,501,733, by replacing residues in substance P sequence by Trp residues. A further class of tachykinin receptor antagonists, comprising a monomeric or dimeric hexa- or heptapeptide unit in linear or cyclic form, is described in GB-A-2216529.

The peptide-like nature of such substances make them too labile from a metabolic point of view to serve as practical therapeutic agents in the treatment of disease. The nonpeptidic antagonists of the present invention, on the other hand, do not possess this drawback, as they are expected to be more stable from a metabolic point of view than the previously-discussed agents.

It is known that in the central nervous system baclofen [β-(aminoethyl)-4-chlorobenzenepropanoic acid] effectively blocks the excitatory activity of substance P, but because in many areas the excitatory responses to other compounds such as acetylcholine and glutamate are inhibited as well, baclofen is not considered a specific substance P antagonist. Pfizer WIPO patent applications (PCT Publication Nos. WO 90/05525, WO 90/05729, WO 91/18899, WO 92/12151 and WO 92/12152) and publications (*Science*, 251,435–437 (1991); *Science*, 251,437–439 (1991); J. Med. Chem., 35, 2591–2600 (1992)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A Glaxo European patent application (EPO Publication No. 0,360,390) discloses various spirolactam-substituted amino acids and peptides which are antagonists or agonists of substance P. A Pfizer WIPO patent application (PCT Publication No. WO 92/06079) discloses fused-ring analogs of nitrogen-containing nonaromatic heterocycles as useful for the treatment of diseases mediated by an excess of substance P. A Pfizer WIPO patent application (PCT Publication No. WO 92/15585 discloses 1-azabicyclo[3.2.2]nonan-3-amine derivatives as substance P antagonists. A Pfizer WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A Sanofi publication (*Life Sci.*, 50, PL101–PL106 (1992)) discloses a 4-phenyl piperidine derivative as an antagonist of the neurokinin A (NK2) receptor.

Howson et al. (*Biorg. & Med. Chem. Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,50.6,673 discloses certain 3-hydroxy quinuclidine compounds as central nervous system stimulants. A Pfizer EPO Patent application (EPO publication 0,436,334) discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al. (*Biorg & Med. Chem. Lett.*, 2 (1), 37–40 (1992)) disclose a fused ring pyrrolidine compound as a substance P antagonist. EPO Publication No. 0,360,390 discloses certain spirolactam derivatives as substance P antagonists. U.S. Pat. No. 4.,804,66discloses certain piperazine compounds as analgesics. U.S. Pat. No. , 4,943,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 94/00440 discloses certain morpholine compounds as substance P antagonists.

Morphological forms of pharmaceutical compounds may be of interest to those involved in the development of a suitable dosage form because if the morphological form is not held constant during clinical and stability studies, the exact dosage used or measured may not be comparable from one lot to the next. Once a pharmaceutical compound is produces for use, it is important to recognize the morphological form delivered in each dosage form to assure that the production process use the same form and that the same amount of drug is included in each dosage. Therefore, it is imperative to assure that either a single morphological form or some known combination of morphological forms is present. In addition, certain morphological forms may exhibit enhanced thermodynamic stability and may be more suitable than other morphological forms for inclusion in pharmaceutical formulations. As used herein, a polymorphic form of a chemical compound is the same chemical entity, but in a different crystalline arrangement.

DETAILED DESCRIPTION OF THE INVENTION

The present invention is directed to a novel polymorphic form of the compound 2-(S)-(3,5-bis(trifluoromethyl)benzyloxy)-4-(3-(5-oxo-1H,4H-1,2,4-triazolo)methyl)-3-(S)-phenyl-morpholine and the process for the preparation of this polymorphic form.

The compound 2-(S)-(3,5-bis(trifluoromethyl)benzyloxy)-4-(3-(5-oxo-1H,4H-1,2,4-triazolo)methyl)-3-(S)-phenyl-morpholine has the structure:

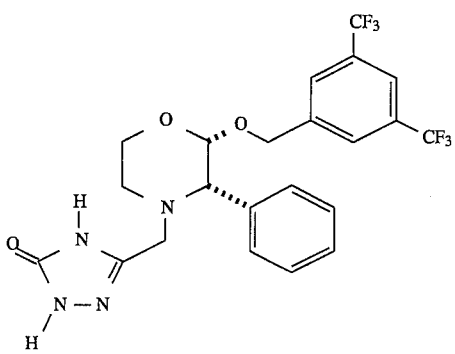

and is a tachykinin receptor antagonist useful in the treatment of inflammatory diseases, pain or migraine, asthma, and emesis.

This particular polymorphic form (herein designated "Form C") has superior properties over other crystalline forms of the compound in that it is thermodynamically more stable than other morphological forms and is more suitable for inclusion in pharmaceutical formulations.

The present invention is also concerned with a process for the preparation of Form C of 2-(S)-(3,5-bis(trifluoromethyl)-benzyloxy)- 4-(3-(5-oxo-1H,4H-1,2,4-triazolo)methyl)-3-(S)-phenyl-morpholine which comprises:

heating a sample of 2-(S)-(3,5-bis(trifluoromethyl)-benzyloxy)- 4-(3-(5-oxo-1H,4H-1,2,4-triazolo)methyl)-3-(S)-phenyl-morpholine of optional morphological composition to a temperature range of 160° to 170° C.; and then returning the sample to ambient temperature.

In particular, the heating of 2-(S)-(3,5-bis(trifluoro-methyl)benzyloxy)- 4-(3-(5-oxo-1H,4H-1,2,4-triazolo)methyl)-3-(S)-phenyl-morpholine may be conducted in a differential scanning calorimetric cell in an open pan at a rate of 1° C./minute under a nitrogen atmosphere and the 2-(S)-(3,5-bis(trifluoromethyl)-benzyloxy)-4-(3-(5-oxo- 1H,4H-1,2,4-triazolo)methyl)-3-(S)-phenyl-morpholine may be heated to a temperature of 160° C., and then cooled to room temperature. Preferably the morphological composition of the starting 2-(S)-(3,5-bis(trifluoro-methyl)benzyloxy)- 4-(3-(5-oxo-1H,4H-1,2,4-triazolo)methyl)- 3-(S)-phenyl-morpholine is Form B.

In addition, the present invention is concerned with an alternative process particularly useful for the preparation of Form C of 2-(S)-(3,5-bis(trifluoromethyl)benzyloxy)-4-(3-(5-oxo-1H,4H-1,2,4-triazolo)methyl)- 3-(S)-phenyl-morpholine on a larger scale comprising:

suspending 2-(S)-(3,5-bis(trifluoromethyl)benzyloxy)-4-(3-(5-oxo-1H,4H-1,2,4-triazolo)methyl)-3-(S)-phenyl-morpholine of optional morphological composition in water;

adding seed crystals of Form C of 2-(S)-(3,5-bis(trifluoromethyl)benzyloxy)- 4-(3-(5-oxo-1H,4H-1,2,4-triazolo)methyl)-3-(S)-phenyl-morpholine;

heating the resultant mixture at 35°–40° C. with stirring for a period sufficient to result in the formation of Form C of 2-(S)-(3,5- bis(trifluoromethyl)benzyloxy)- 4-(3-(5-oxo-1H,4H-1,2,4-triazolo)-methyl)- 3-(S)-phenyl-morpholine; and collecting the resultant Form C of 2-(S)-(3,5-bis(trifluoromethyl)benzyloxy)- 4-(3-(5-oxo-1H, 4H-1,2,4-triazolo)methyl)-3-(S)-phenyl-morpholine.

Similarly, the present invention is also directed to a process for the preparation of morphologically homogeneous 2-(S)-(3,5-bis(trifluoromethyl)benzyloxy)- 4-(3-(5-oxo-1H,4H-1,2,4-triazolo)methyl)- 3-(S)-phenyl-morpholine, comprising any of the aforementioned processes.

The compound of this invention, the novel polymorphic form of 2-(S)-(3,5-bis(trifluoromethyl)benzyloxy)-4-(3-(5-oxo-1H,4H-1,2,4-triazolo)methyl)-3-(S)-phenyl-morpholine, is a tachykinin receptor antagonists useful in the treatment of inflammatory diseases, pain or migraine, asthma, and emesis. Accordingly, the present invention is further concerned with pharmaceutical formulations comprising this polymorphic form as an active ingredient, and the use of this polymorphic form and its formulations in the treatment of certain disorders.

Form C of 2-(S)-(3,5-bis(trifluoromethyl)benzyloxy)-4-(3-(5-oxo-1H,4H-1,2,4-triazolo)methyl)-3-(S)-phenyl-morpholine is anhydrous and non-hygroscopic and exhibits a high degree of thermal stability as a neat solid and in hydroalcoholic solution.

Form A is an anhydrous crystalline material melting at 254° C. which is obtained directly from recrystallization in the chemical synthesis of 2-(S)-(3,5-bis(trifluoromethyl)benzyloxy)-4-(3-(5-oxo-1H,4H-1,2,4-triazolo)methyl)-3-(S)-phenyl-morpholine.

Form B is a hydrated material that is obtained from an aqueous suspension of Form A at room temperature. Form B is a metastable hydrated form and is converted to Form C either thermally, or by adding Form C seed crystals to a suspension of Form B.

From C may be obtained directly from Form A by seeding an aqueous suspension of Form A. An aqueous suspension of Form A spontaneously converts to the higher melting polymorph Form C if a few seed crystals of Form C are present. Form C may also be prepared on a small scale by heating a sample of 2-(S)-(3,5-bis(trifluoromethyl)benzyloxy)- 4-(3-(5-oxo-1H,4H-1,2,4-triazolo)methyl)-3-(S)-phenyl-morpholine of optional morphological composition to a temperature range of 160° to 170° C., and returning the sample to ambient temperature.

Differential Scanning Calorimeteric Cell [DSC]

Form C of 2-(S)-(3,5-bis(trifluoromethyl)benzyloxy)-4-(3-(5-oxo-1H,4H-1,2,4-triazolo)methyl)-3-(S)-phenyl-morpholine was prepared by heating Form A of 2-(S)-(3,5-bis(trifluoromethyl)benzyloxy)- 4-(3-(5-oxo-1H,4H-1,2,4-triazolo)methyl)-3-(S)-phenyl-morpholine (prepared as described in Example 1) in a differential scanning calorimetric (DSC) cell in an open pan to 160° C. at a heating rate of 1° C./min under a nitrogen atmosphere.

The DSC curve of Form A at 5° C./min shows onset of a melting endotherm at 153° C., followed by a peak melting endotherm at 156° C. The DSC curve of Form B at 1° C./min shows thermal events due to water loss, a melting endotherm at 143° C., followed by a recrystallization exotherm at 147° C., and a melting endotherm at 179° C.

TABLE 1

DSC Data [samples heated at a rate of 5° C./min under nitrogen atmosphere (extrapolated onset temperature)]

| | m.p. (°C.) |
|---|---|
| Form A | 153–155 |
| Form B | ca. 145 |
| Form C | 176–178 |

X-Ray Powder Diffraction (XRPD)

X-Ray powder diffraction studies have been widely used to elucidate molecular structures, crystallinity and polymorphism. X-ray powder diffraction (XRPD) patterns were recorded using a Siemens D-5000 instrument equipped with a 3 kw X-ray generator (CuKα1 radiation) and a NaI (Ti) scintillation detector. Measurements were made from 3° to 45° (2 theta) with the sample maintained at ambient room temperature.

Form A was characterized by an X-ray powder diffraction pattern with reflections at approximately: 7.7°, 9.5°, 12.7°, 14.0°, 14.5°, 15.3°, 15.9°, 17.4°, 18.1°, 19.4°, 20.5°, 22.3°, 22.9°, 23.8°, 24.9°, and 26.5° (2 theta).

Form B was characterized by an X-ray powder diffraction pattern with reflections at approximately: 17.7°, 18.7°, 19.3°, 20.2°, 21.8°, and 24.2° (2 theta).

Form C was characterized by an X-ray powder diffraction pattern with reflections at approximately: 11.5°, 12.6°, 15.5°, 16.8°, 20.1°, 21.3°, 25.4° and 28.5° (2 theta).

These XRPD patterns confirm that all three samples are distinct crystalline forms.

Microscopy

Examination of the polymorphic forms was conducted at 10033 magnification under plain and polarized light. Forms A and B consisted of irregularly shaped particles with an average size of about 50 μm. Form C was observed to consist of needle shaped particles averaging about 20–30 μm in length. All the samples appeared birefringent under polarized light.

Hygroscopicity

The total volatiles content (as established by TGA analysis) of solid samples of Form A and C upon exposure to various controlled humidities is tabulated below.

TABLE 2

| Total Volatiles Content of Form A and Form C: | | |
| --- | --- | --- |
| % RH | Form A | Form C |
| 0 | 0.2 | 0.5 |
| 11 | 0.3 | 0.4 |
| 33 | 0.2 | 0.4 |
| 47 | 0.2 | 0.3 |
| 76 | 0.3 | 0.7 |
| 100 | 0.4 | 0.9 |

This data indicates that both Form A and Form C are essentially non-hygroscopic over the entire range of relative humidities. TGA of Form B reveals a 2.1% weight loss (corresponding to 0.60 moles water) commencing at about 60° C.

Solubility

Form A is soluble to the extent of 5 μg/mL in distilled water at room temperature. The aqueous solubility of Form C was determined to be 2.7 μg/mL in distilled water at room temperature.

TACHYKININ ANTAGONISM ASSAY

The compound of this invention, the polymorphic Form C of 2-(S)-(3,5-bis(trifluoromethyl)benzyloxy)-4-(3-(5-oxo-1H,4H-1,2,4-triazolo)methyl)- 3-(S)-phenyl-morpholine, is useful for antagonizing tachykinins, in particular substance P and neurokinin A in the treatment of gastrointestinal disorders, central nervous system disorders, inflammatory diseases, pain or migraine, asthma, and emesis in a mammal in need of such treatment. This activity may be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_{12}$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10 % fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}I$-substance P ($^{125}I$-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0,004 mg/ml leupeptin, 0.2 mg/ml BSA, 0.01 mM phosphoramidon) such that 200 ul of the cell suspension would give rise to about 10,000 cpm of specific $^{125}I$-SP binding (approximately 50,000 to 200,000 cells). In the binding assay, 200 ul of cells were added to a tube containing 20 ul of 1.5 to 2.5 nM of $^{125}I$-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3H$-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The compound of the present invention is useful in the prevention and treatment of a wide variety of clinical conditions which are characterized by the presence of an excess of tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis, asthma, and bronchospasm; airways disease modulated by neurogenic inflammation; diseases associated with decreased glandular secretions, including lacrimation, such as Sjogren's syndrome, hyperlipoproteinemias IV and V, hemochromatosis, sarcoidosis, or amyloidosis; inflammatory diseases such as inflammatory bowel disease, psoriasis, fibrositis, ocular inflammation, osteoarthritis, rheumatoid arthritis, pruritis, and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression, such as systemic lupus erythmatosus; gastrointestinal (GI) disorders and diseases of the GI tract such as disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, chronic pain or that attributable to or associated with any of the foregoing conditions especially the transmission of pain in migraine. Hence, the compound may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compound of the present invention is also of value in the treatment of a combination of the above conditions, in particular in the treatment of combined post-operative pain and post-operative nausea and vomiting.

The compound of the present invention is particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, this compound is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compound of the present invention is also of use in the treatment of emesis induced by radiation including radiation therapy such as in the treatment of cancer, or radiation sickness, and in the treatment of post-operative nausea and vomiting.

The compound of the present invention are also of use in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

As calcium channel blocking agents the compound of the present invention is useful in the prevention of treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, this compound may be capable of lowering elevated intraocular pressure when administered topically to the hypertensive eye in solution in a suitable ophthalmic vehicle. Also, this compound may be useful in the reversal of multidrug resistance in tumor cells by enhancing the efficacy of chemotherapeutic agents. In addition, the compound may have activity in blocking calcium channels in insect brain membranes and so may be useful as insecticides.

The compound of the present invention is particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; asthma; osteoarthritis; rheumatoid arthritis; and especially migraine. The compound of the present invention is also particularly useful in the treatment of diseases characterized by neurogenic mucus secretion, especially cystic fibrosis.

In the treatment of the clinical conditions noted above, the compound of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more forms of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which may be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, microcrystalline cellulose, stearic acid, dicalcium phosphate or gums, and other pharmaceutical diluents, to form a solid composition containing a homogeneous mixture of a compound of the present invention, or a non-toxic pharmaceutically acceptable salt thereof. When referring to these mixtures as homogeneous, it is meant that the active ingredient is dispersed evenly throughout the composition so that the composition may be readily subdivided into equally effective unit dosage forms such as tablets, pills and capsules. This solid mixture is then subdivided into unit dosage forms of the type described above containing from 0.1 to about 500 mg of the active ingredient of the present invention. The tablets or pills of the novel composition may be coated or otherwise compounded to provide a dosage form affording the advantage of prolonged action. For example, the tablet or pill may comprise an inner dosage and an outer dosage component, the latter being in the form of an envelope over the former. The two components may be separated by an enteric layer which serves to resist disintegration in the stomach and permits the inner component to pass intact into the duodenum or to be delayed in release. A variety of materials may be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavored syrups, and aqueous or oil suspensions, and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized suspensions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ the compound of the present invention in conjunction with another pharmacologically active agent. For example, the compound of the present invention may be presented together with another therapeutic agent as a combined preparation for simultaneous, separate, or sequential use for the relief of emesis. Such combined preparations may be, for example, in the form of a twin pack. A preferred combination comprises the compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

Similarly, for the treatment of respiratory diseases, such as asthma, the compound of the present invention may be used in conjunction with a bronchodilator, such as a $\beta_2$-adrenergic receptor agonist or a tachykinin antagonist which acts at neurokinin-2 receptors. Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, the compound of the present invention may be used in conjunction with a tachykinin antagonist which acts at neurokinin-2 receptors, or with tachykinin receptor antagonist which acts at both neurokinin-1 and neurokinin-2 receptors. Similarly, for the prevention or treatment of emesis the compound of the present invention may be used in conjunction with other anti-emetic agents, especially $5HT_3$ receptor antagonists, such as ondansetron, granisetron, tropisetron, decadron, and zatisetron. Likewise, for the prevention or treatment of migraine the compound of the present invention may be used in conjunction with other anti-migraine agents, such as ergotamines or $5HT_1$ agonists, especially sumatriptan. For the prevention or treatment of inflammatory conditions in the lower urinary tract, especially cystitis, the compound of the present invention may be used in conjunction with an antiinflammatory, such as a bradykinin receptor antagonist. The compound of the present invention and the other pharmacologically active agent may be administered to a patient simultaneously, sequentially or in combination.

The compound of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neruotransmission of pain sensations, a suitable dosage level is about 0.001 to 25 mg/kg per day, preferably about 0.05 to 10 mg/kg per day, and especially about 0.1 to 5 mg/kg per day. The compound may be administered on a regimen of 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.01 to 1 mg/kg per day. The compound may be administered on a regimen of 1 to 4 times per day, preferably once or twice per day.

Methods for preparing the polymorphic form of this invention are illustrated in the following Examples. The following examples are given for the purpose of illustrating the present invention and shall not be construed as being limitations on the scope or spirit of the instant invention.

EXAMPLE1

2-(S)-(3,5-Bis(trifluoromethyl)benzyloxy)-4-(3-(5-oxo-1H,4H-1,2,4-triazolo)methyl)-3-(S)-phenyl-morpholine N-Methylcarboxy-2-chloroacetamidrazone
Step A: N-Methylcarboxy-2-chloroacetamidrazone A solution of 5.0 g (66.2 mmol) of chloroacetonitrile in 35 mL of dry methanol was cooled to 0° C. and was treated with 0.105 g (1.9 mmol) of sodium methoxide. The ice-bath was removed and the mixture was allowed to stir at room temperature for 30 minutes. To the reaction was then added 0.110 mL (1.9 mmol) of acetic acid and then 5.8 g (64.9 mmol) of methyl hydrazinecarboxylate. After stirring 30 minutes at room temperature, the suspension was concentrated in vacuo, and placed on the high-vac line overnight, to give 10.5 g (98%) of a yellow powder.
$^1$H NMR (CD$_3$OD, 400 MHz, ppm): δ3.71 (s, 3H), 4.06 (s, 2H).
Step B: 3,5-Bis(trifluoromethyl)benzyl alcohol, trifluoromethane-sulfonate ester A solution of 1.00 g (4.1 mmole) of 3,5-bis(trifluoromethyl)benzyl alcohol and 1.05 g (5.12 mmole) of 2,6-di-t-butyl-4- methylpyridine in 45 mL of dry carbon tetrachloride under a nitrogen atmosphere was treated with 0.74 mL (4.38 mmole) of trifluoromethanesulfonic anhydride at room temperature. A white precipitate formed shortly after the addition of the anhydride. After 90 min, the slurry was filtered under nitrogen with a Schlenk filter, and the filtrate was concentrated in vacuo. The residue, which was a two-phase oil, was dissolved under nitrogen in 10 mL of dry toluene. The resulting clear solution was used immediately in Step E below.
Step C: N-Benzyl-(S)-phenylglycine A solution of 1.51 g (10.0 mmol) of (S)-phenylglycine in 5 mL of 2N aqueous sodium hydroxide solution was treated with 1.0 mL (10.0 mmol) of benzaldehyde and stirred at room temperature for 20 minutes. The solution was diluted with 5 mL of methanol, cooled to 0° C., and carefully treated with 200 mg (5.3 mmol) of sodium borohydride. The cooling bath was removed and the reaction mixture was stirred at room temperature for 1.5 hours. The reaction was diluted with 20 mL of water and extracted with 2×25 mL of methylene chloride. The aqueous layer was acidified with concentrated hydrochloric acid to pH 6 and the solid that precipitated was filtered, washed with 50 mL of water, 50 mL of 1:1 v/v methanol/ethyl ether and 50 mL of ether, and dried to afford 1.83 g (76%) of product, mp 230°–232° C.
Analysis Calcd for C$_{15}$H$_{15}$NO$_2$: C, 74.66; H, 6.27; N, 5.81. Found: C, 74.17;H, 6.19; N, 5.86.
Step D: 3-(S)-Phenyl-4-benzyl-2-morpholinone A mixture of 4.00 g (16.6 mmol) of N-benzyl-(S)-phenylglycine, 5.00 g (36.0 mmol) of potassium carbonate, 10.0 mL of 1,2-dibromoethane and 25 mL of N,N-dimethylformamide was stirred at 100° C. for 20 hours. The mixture was cooled and partitioned between 200 mL of ethyl ether and 100 mL of water. The layers were separated and the organic layer was washed with 3×50 mL of water, dried over magnesium sulfate and concentrated in vacuo. The residue was purified by flash chromatography on 125 g of silica gel eluting with 9:1 v/v, then 4:1 v/v hexanes/ethyl ether to afford 2.41 g (54%) of the product as a solid, mp 98°–100° C.
Mass Spectrum (FAB): m/Z 268 (M+H, 100%). $^1$H NMR (CDCl$_3$, 200 MHz, ppm): δ2.54–2.68 (m, 1H), 2.96 (dt, J=12.8, 2.8, 1H), 3.14 (d, J=13.3, 1H), 3.75 (d, J=13.3, 1H), 4.23 (s, 1H), 4.29–4.37 (m, 1H), 4.53 (dt, J=3.2, 11.0), 7.20–7.56 (m, 10H). Analysis Calcd for $C_{17}H_{17}NO_2$: C, 76.38; H, 6.41; N, 5.24. Found: C, 76.06; H, 6.40; N, 5.78.

Step E: 4-Benzyl-2-(S)-(3,5-bis(trifluoromethyl)benzyloxy)-3-(S)-phenylmorpholine A solution of 0.500 g (1.87 mmole) of N-benzyl-3-(S)-phenylmorpholin- 2-one in 10 mL of dry THF was cooled to −75° C. under nitrogen and was treated dropwise with 2.06 mL (2.06 mmole) of a 1M solution of lithium tri(sec-butyl)-borohydride (L-Selectride®) in THF. After stirring the solution at −75° C. for 30 min, a solution of 3,5-bis(trifluoromethyl)benzyl alcohol, trifluoromethanesulfonate ester in toluene was added by cannula so that the internal temperature was maintained below −60° C. The resulting solution was stirred at −75° C. for 1 hr and then between −38° C. and −50° C. for 2 hr. The solution was then poured into a mixture of 25 mL of ethyl acetate and 20 mL of saturated aqueous sodium bicarbonate, and the layers were separated. The aqueous phase was extracted with 2×30 mL of ethyl acetate, the combined organic layers were dried over sodium sulfate, the mixture was filtered and the filtrate concentrated in vacuo. The residue was purified by flash chromatography on 130 g of silica eluting with 2L of 100:5 hexanes:ethyl acetate to give 0.68 g (73%) of an oil, which by $^1$H NMR is a 20:1 mixture of cis:trans morpholines.

1H NMR (CDCl$_3$, 400 MHz, ppm): δmajor (cis) isomer: 2.37 (td, J=12, 3.6, 1H), 2.86 (app t, J=13, 2H), 3.57 (d, J=2.6, 1H), 3.63 (dq, J=11.3, 1,6, 1H), 3.89 (d, J=13.3, 1H), 4.12 (td, J=11.6, 2.4, 1H), 4.40 (d, J=13.6, 1H), 4.69 (d, J=2.9, 1H), 4.77 (d, J=13.6, 1H), 7.2–7.4 (m, 8H), 7.43 (s, 2H) 7.55 (br d, 2H), 7.69 (s, 1H).

Step F: 2-(S)-(3,5-Bis(trifluoromethyl)benzyloxy)-3-(S)-phenyl-morpholine

A mixture of 0.68 g (1.37 mmole) of 4-benzyl-2-(S)-(3, 5-bis(trifluoromethyl)benzyloxy)- 3-(S)-phenyl-morpholine and 280 mg of 10% Pd/C in 36 mL of 97:3 ethanol:water was stirred under one atmosphere of hydrogen for 15 hr. The mixture was filtered through Celite, the filter cake was washed generously with ethanol, and the filtrated was concentrated in vacuo. The residue was purified by flash chromatography on 68 g of silica eluting with 1L of 33:67 hexanes: diethyl ether, then 1L of 25:75 hexanes:diethyl ether to give 0.443 g (80%) of an oil, which by 1H NMR was pure cis morpholine.

1H NMR (CDCl$_3$, 400 MHz, ppm): δ1.8 (br s, 1H), 3.10 (dd, J=12.5, 2.9, 1H), 3.24 (td, J=12.2, 3.6, 1H), 3.62 (dd, J=11.3, 2.5, 1H), 4.04 (td, J=11.7, 3, 1H), 4.11 (d, J=2.4, 1H), 4.49 (d, J=13.5, 1H), 4.74 (d, J=2.5, 1H), 4.80 (d, J=13.3, 1H), 7.25–7.40 (m, 5H), 7.40 (s, 2H), 7.68 (s, 1H). Analysis Calcd for $C_{19}H_{17}F_6NO_2$: C, 56.30; H, 4.23; N, 3.46 ; F, 28.12. Found: C, 56.20; H, 4.29 ; N, 3.34; F, 27.94.

Step G: 4-(2-(N-Methylcarboxy-acetamidrazono)-2-(S)-(3, 5-bis(trifluoromethyl)benzyloxy)- 3-(S)-phenyl-morpholine A solution of 2.30 g (5.7 mmol) of 2-(S)-(3,5-bis(trifluoromethyl)benzyloxy)- 3-(S)-phenyl-morpholine, 1.13 g (6.8 mmol) of N-methylcarboxy-2-chloroacteamidrazone, and 1.50 mL (8.6 mmol) N,N-diisopropylethylamine in 25 mL of acetonitrile was stirred at room temperature for 20 hours. The product, which had preciptated, was filtered, washed with 5 mL of ice cold acetonitrile and dried to give 1.83 g of a white solid. The filtrate was concentrated in vacuo and the residue was partitioned between 50 mL of methylene chloride and 20 mL of water. The layers were separated and the organic layer was dried over magnesium sulfate. The aqueous layer was extracted with 50 mL of methylene chloride; the extract was dried, combined with the original organic layer, and the combined organics were concentrated in vacuo. The residue was purified by flash chromatography on 30 g of silica gel eluting with 50:1:0.1 v/v/v methylene chloride/methanol/ammonium hydroxide to afford an additional 1.09 g of product (96% total).

Mass Spectrum (FAB): m/Z 535 (M+H, 100%), 462 (16%), 291 (30%), 226 (35%), 173 (25%).

$^1$H NMR (CDCl$_3$, 400 MHz, ppm): δ2.53 (dt, J=3.5, 12.2, 1H), 2.59 (d, J=14.6, 1H), 2.94 (d, J=11.8, 1H), 3.37 (d, J=14.6, 1H), 3.58 (d, J=2.8, 1H), 3.62–3.72 (m, 1H), 3.75 (s, 3H), 4.16 (dt, J=2.2, 11.8, 1H), 4.44 (d, J=13.2, 1H), 4.70 (d, J=2.8, 1H), 4.79 (d, J=13.2), 5.55 (br s, 2H), 7.30–7.46 (m, 7H), 7.72 (s, 1H).

Step H: 2-(S)-(3,5-Bis(trifluoromethyl)benzyloxy)-4-(3-(5-oxo- 1H,4H-1,2,4-triazolo)methyl)- 3-(S)-phenyl-morpholine A solution of 2.89 g (5.4 mmol) of 4-(2-(N-methylcarboxyacetamidrazono)-2-(S)-(3,5-bis(trifluoromethyl) benzyloxy)-3-(S)-phenyl-morpholine (from Step B) in 36 mL of xylenes was heated at reflux for 1.5 hours. The solution was cooled and concentrated in vacuo. The residue was taken up in 50 mL of 3:1 v/v hexanes/ethyl acetate which caused crystallization of the product. The product was filtered and dried to afford 1.85 g of a solid. Recrystallization of the solid from 30 mL of 4:1 v/v hexanes/ethyl acetate afforded 1.19 g of pure product as a white solid. All of the crystallization liquors were combined and concentrated in vacuo. The residue was purified by flash chromatography on 30 g of silica gel eluting with 50:1:0.1 v/v/v methylene chloride/methanol/ammonium hydroxide to afford an additional 0.69 g of a solid. Three recrystallizations from 20 mL of 4:1 v/v hexanes/ethyl acetate afforded an additional 0.39 g of 2-(S)-(3,5-bis(trifluoromethyl)benzyloxy)- 4-(3-(5-oxo-1H,4H-1, 2,4-triazolo)methyl)- 3-(S)-phenyl-morpholine as a white solid (58% total) (mp=156°–157° C.; designated "Form A").

Mass Spectrum (FAB): m/Z 503 (M+H), 259 (55%), 226 (40%), 160 (3%). $^1$H NMR (CDCl$_3$, 400 MHz, ppm): δ2.57 (app t, J=9.6, 1H), 2.87–2.97 (m, 2H), 3.58–3.71 (m, 3H), 4.18 (app t, J=10.4, 1H), 4.46 (d, J=13.6), 4.68 (d, J=2.8, 1H), 4.85 (d, J=13.6, 1H), 7.30–7.45 (m, 7H), 7.64 (s, 1H), 10.40 (br s, 1H), 10.73 (br s, 1H).

EXAMPLE 2

Preparation of Form B of 2-(S)-(3,5-Bis(trifluoromethyl)benzyloxy)-4-(3-(5-oxo-1H,4H-1,2,4-triazolo)methyl)-3-(S)-phenyl-morpholine Form A of 2-(S)-(3,5-bis(trifluoromethyl)benzyloxy)-4-(3-(5-oxo-1H,4H-1,2,4-triazolo)methyl)-3-(S)-phenyl-morpholine was suspended in 40 ml of deionized water and the resultant mixture was sonicated for approximately 1 minute, then stirred at room temperature for 48 hours. The mixture was transferred to a centrifuge tube and spun at 2,700 G for 20 minutes. The supernatant was removed and the solid was placed on a piece of filter paper and allowed to air-dry for 4 days.

EXAMPLE 3

Preparation of Seed Crystals of Form C of 2-(S)-(3,5-Bis(trifluoromethyl)benzyloxy)-4-(3-(5-oxo-1H,4H-1,2,4-triazolo)methyl)-3-(S)-phenyl-morpholine A 3.0 mg sample of Form B of 2-(S)-(3,5-bis(trifluoromethyl)benzyloxy)-4-(3-(5-oxo-1H,4H-1,2,4-triazolo)methyl)-3-(S)-phenyl-morpholine was placed in a small aluminum pan and the unsealed pan was placed in a Differential Scanning Calorimeteric Cell (DSC) instrument. The sample was heated at 1 °C./min under an inert nitrogen atmosphere from ambient temperature to 160° C., then cooled back down to room temperature. The resulting solid is suitable for use as seed crystals in the large-scale preparation of Form C of 2-(S)-(3,5-bis(trifluoro-methyl)benzyloxy)- 4-(3-(5-oxo-1H,4H-1,2,4triazolo)methyl)- 3-(S)-phenyl-morpholine.

EXAMPLE 4

Preparation of Form C of 2-(S)-(3,5-Bis(trifluoromethyl)benzyloxy)-4-(3-(5-oxo-1H,4H-1,2,4-triazolo)methyl)-3-(S)-phenyl-morpholine Form A of 2-(S)-(3,5-bis(trifluoromethyl)benzyloxy)-4-(3-(5-oxo-1H,4H-1,2,4-triazolo)methyl)-3-(S)-phenyl-morpholine was suspended in 40 ml of deionized water and the resultant mixture was vigorously stirred at room temperature. A few seed crystals of Form C of 2-(S)-(3,5-bis(trifluoromethyl)benzyloxy)-4-(3-(5-oxo-1H,4H-1,2,4-triazolo)methyl)- 3-(S)-phenyl-morpholine were added and the mixture was heated to 40° C. Stirring was continued for 18 hours, then the mixture was cooled to ambient temperature, and the resultant solid was collected by filtration. The collected solid was air-dried on a piece of filter paper for 30 minutes.

EXAMPLE 5

Typical Pharmaceutical Compositions Containing the Compound of the Invention

| A: Dry Filled Capsules Containing 5 mg of Active Ingredient Per Capsule | |
|---|---|
| Ingredient | Amount per capsule (mg) |
| Active ingredient | 5 |
| Lactose | 194 |
| Magnesium stearate | 1 |
| Capsule (size No. 1) | 200 |

The active ingredient may be reduced to a No. 60 powder and the lactose and magnesium stearate may then be passed through a No. 60 blotting cloth onto the powder. The combined ingredients may then be mixed for about 10 minutes and filled into a No. 1 dry gelatin capsule.

B: Tablet

A typical tablet would contain the active ingredient (5 mg), pregelatinized starch USP (82 mg), microcrystalline cellulose (82 mg) and magnesium stearate (1 mg).

C: Suppository

Typical suppository formulations for rectal administration contain the active ingredient (0.08–1.0 mg), disodium calcium edetate (0.25–0.5 mg), and polyethylene glycol (775–1600 mg). Other suppository formulations may be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A polymorphic form of the compound 2-(S)-(3,5-bis(trifluoromethyl)-benzyloxy)- 4-(3-(5-oxo-1H,4H-1,2,4-triazolo)methyl)- 3-(S)-phenyl-morpholine designated Form C, which is characterized by an endotherm of melting at an extrapolated onset temperature of 176°–178° C. when heated in a differential scanning calorimetric cell at a rate of 5° C./min under a nitrogen atmosphere, which is characterized by an X-ray powder diffraction pattern with reflections at approximately: 11.5°, 12.6°, 15.5°, 16.8°, 20.1°, 21.3°, 25.4° and 28.5° (2 theta), and which is characterized by an aqueous solubility of 2.7 μ/mL in distilled water at room temperature.

2. A pharmaceutical composition comprising a pharmaceutically acceptable carrier and an effective amount of the polymorphic form of claim 1.

* * * * *